US009364363B2

(12) United States Patent
Cropper (10) Patent No.: US 9,364,363 B2
(45) Date of Patent: *Jun. 14, 2016

(54) ANKLE CONTROL SYSTEM AND METHOD (76) Inventor: Dean E. Cropper, Ashland, OR (US)

( * ) Notice: Subject to any disclaimer, the term of this patent is extended or adjusted under 35 U.S.C. 154(b) by 564 days.

This patent is subject to a terminal disclaimer.

(21) Appl. No.: 11/541,604

(22) Filed: Oct. 3, 2006

(65) Prior Publication Data

US 2007/0060854 A1 Mar. 15, 2007

Related U.S. Application Data (63) Continuation of application No. 10/133,636, filed on Apr. 29, 2002, now Pat. No. 7,115,105.

(51) Int. Cl.
A61F 5/00 (2006.01)
A61F 5/01 (2006.01)

(52) U.S. Cl.
CPC .................... A61F 5/0111 (2013.01)

(58) Field of Classification Search
CPC ............... A61F 13/066; A61F 5/0111
USPC ............ 602/23–27, 60–62; 128/882
See application file for complete search history.

(56) References Cited

U.S. PATENT DOCUMENTS

| 2,800,900 | A | 7/1957 | Schultz |
| 4,085,746 | A | 4/1978 | Castiglia |
| 4,280,488 | A | 7/1981 | Polsky et al. |
| 4,280,489 | A | 7/1981 | Johnson, Jr. |
| 4,313,433 | A | 2/1982 | Cramer |
| 4,323,058 | A | 4/1982 | Detty |
| 4,367,733 | A | 1/1983 | Stromgren |
| 4,590,932 | A | 5/1986 | Wilkerson |
| 4,597,395 | A | 7/1986 | Barlow et al. |
| 4,621,648 | A | 11/1986 | Ivany |
| 4,628,945 | A | 12/1986 | Johnson, Jr. |
| 4,640,025 | A | 2/1987 | DeRenzo |
| 4,651,726 | A | 3/1987 | Holland |
| 4,724,847 | A | 2/1988 | Nelson |
| 4,729,370 | A | 3/1988 | Kallassy |
| 4,844,058 | A | 7/1989 | Vogelbach |
| 4,878,504 | A | 11/1989 | Nelson |
| 5,039,093 | A | 8/1991 | Collier |
| 5,050,620 | A | 9/1991 | Cooper |
| 5,067,486 | A | 11/1991 | Hely |
| 5,099,860 | A | 3/1992 | Amrein |
| 5,125,400 | A | 6/1992 | Johnson, Jr. |
| 5,330,419 | A | 7/1994 | Toronto et al. |
| 5,399,155 | A | 3/1995 | Strassburg |
| 5,620,413 | A | 4/1997 | Olson |
| 5,676,641 | A * | 10/1997 | Arensdorf et al. .............. 602/27 |
| 5,735,807 | A | 4/1998 | Cropper |
| 5,755,679 | A | 5/1998 | Selner et al. |
| 5,795,316 | A * | 8/1998 | Gaylord .......................... 602/27 |
| 5,899,872 | A | 5/1999 | Gilmour |
| 6,109,267 | A | 8/2000 | Shaw et al. |
| 6,117,098 | A | 9/2000 | Weber et al. |
| 6,602,216 | B1 | 8/2003 | Nordt |
| 6,652,474 | B1 | 11/2003 | Quinn et al. |
| 7,354,413 | B2 | 4/2008 | Fisher |

* cited by examiner

Primary Examiner — Michael A. Brown
(74) Attorney, Agent, or Firm — Durham Jones & Pinegar Intellectual Property Law Group (57) ABSTRACT An ankle control system, having a form-fitting sock or brace, a relatively-rigid support member, a lever motion stabilizing strap, and collar. The form-fitting sock or brace has opposing medial and lateral sides, a foot portion having an arch portion, and an ankle portion having an upper attachment element. The relatively-rigid support member is connected to the form-fitting sock or brace and contours about a wearer's leg. The lever motion stabilizing strap acts as a lasso to restrict inversion, eversion, and plantar flexion/inversion through the lever action of the foot with respect to the ankle.

33 Claims, 6 Drawing Sheets

ANKLE CONTROL SYSTEM AND METHOD

CROSS-REFERENCE TO RELATED APPLICATION

This application is a CONTINUATION APPLICATION of prior U.S. patent application Ser. No. 10/133,636, filed Apr. 29, 2002, titled "Ankle Control System," and issued as U.S. Pat. No. 7,115,105, hereby incorporated by reference in its entirety.

FIELD OF THE INVENTION

The present invention relates to an ankle control system and, more particularly, to an ankle control system, that provides superior yet comfortable support while allowing at least a substantial range of movement required for walking, running, and jumping. The present invention also relates to a method for controlling an ankle.

BACKGROUND OF THE INVENTION

Ankle sprains, contusions, arthritis, and tendonitis are common occurrences. For example, one of the most common causes for sprains is overextension of an ankle during athletic activity. Of course, numerous other situations exist where ankle injury is sustained. As such, for athletes and non-athletes alike, a need exists for an effective, comfortable ankle support, both to prevent and to help remedy these various ankle injuries. There are three common types of sprains—1) inversion, whereby the foot folds inwardly, 2) eversion, whereby the foot folds outwardly, and 3) plantar flexion/inversion, whereby the foot folds both inwardly and downwardly. The first and third of these types of injuries is made particularly painful because of damage to the ligament controlling the lever motion of the foot with respect to the ankle, which occurs during plantar-flexion and dorsi-flexion, the two movements necessary for walking, running, and jumping.

Certain types of sprains are further characterized as "high," depending on the ligament or ligaments affected. Individual ankles and types of sprains vary and must be treated and prevented accordingly to achieve a desired effect, which depends on the relative positioning of the support applied. For example, many sprains often affect multiple ligaments, and thus call for support accounting for each affected ligament. For example, during treatment once one ligament has healed, efforts to remedy a sprain should be focused on supporting any other ligament still affected. Moreover, individual ankle sizes and shapes vary from individual to individual and therefore respond differently to various positioning of support.

Heretofore several attempts have be made to provide adequate and comfortable support to remedy or prevent these types of injuries.

For example, U.S. Pat. No. 5,067,486 issued to Hely ("Hely") relates to a boot-like body member having a pair of stabilizing straps both fixedly attached at the rear of an ankle in one particular, immovable position. This configuration does not allow for adjustable positioning of these straps in accordance with various types of sprains, and further requires two straps, which do not tighten as effectively as a single strap around the rear portion of the boot. Hely fails to account for the various positions of sprains along the vertical length of the ankle, and includes no mechanism directed to controlling foot-ankle lever motion.

U.S. Pat. No. 4,729,370 issued to Kallassy ("Kallassy") relates to an ankle support having a lateral strap, a medial strap, and a lateral strap. Kallassy also fails to provide adjustable positioning accounting for the height of a sprain, and is ineffective in providing lever motion control. Kallassy's lateral strap is attached only to the lateral side of the ankle. Kallassy therefore does not provide an effective way of controlling the lever motion of the foot.

It is therefore an object of the present invention to remedy the defects of prior ankle control systems, and, in particular, to provide an ankle control system that is lightweight, easy to wear and effective.

An additional object of the present invention is to provide an ankle control system that affords control over the lever action, i.e., lever motion, of a foot to remedy and prevent plantar flexion/inversion.

SUMMARY OF THE INVENTION

In accordance with the above objects, one embodiment of the present invention provides an ankle control system, comprising: a form-fitting sock, a relatively-rigid support member, and a lever motion stabilizing strap. The form-fitting sock has opposing medial and lateral sides, opposing front and back sides, a foot portion having an arch portion, and an ankle portion having an upper attachment portion. The relatively-rigid support member contours about the leg of the wearer and is connected to the upper attachment element of the form-fitting sock. The lever motion stabilizing strap has a first end removably attachable to the foot portion of the form-fitting sock. This lever motion stabilizing strap is circumferentially wrapable around the foot portion to securely attach to the first end, and has a second end adjustably attachable to one of the lateral and medial sides. The lever motion stabilizing strap forms a circumferential restraint around the entire foot portion, which allows effective lever motion control of a foot.

According to another embodiment of the invention, a single, straight and taut length of the lever motion stabilizing strap operatively spans between the foot portion and the upper attachment portion to provide lever motion restraint.

According to a still further embodiment, the ankle control system comprises an elastic collar, which is part of the upper attachment element, securing the second end of the lever motion stabilizing strap to the form-fitting sock.

According to yet another embodiment, the form-fitting sock comprises a laminate material no greater than about 0.025" to 0.045" thickness and comprising a polyurethane membrane no greater than about 0.001" thickness and a stretchable material covering said membrane. The material, in a stretched state, has the property of low active compressibility force and strong passive resistance to expansion substantially greater than the compressibility force.

According to a still further embodiment, the lever motion stabilizing strap is attachable to the form-fitting sock by a hook and loop material.

According to yet another embodiment, the first end of the lever motion stabilizing strap comprises either hook or loop material on one side for attachment to the form-fitting sock, and either hook or loop material on a second side for attachment to a mid-portion of the lever motion stabilizing strap once the lever motion stabilizing strap is wrapped around the foot portion.

According to a still further embodiment, the lever motion stabilizing strap is operatively configured as a lasso to restrict plantar flexion or plantar inversion through the lever action of a foot with respect to an ankle.

According to yet another embodiment, the first end of the lever motion stabilizing strap is tapered.

According to a still further embodiment, the lever motion stabilizing strap comprises at least one pull-loop.

According to yet another embodiment, the ankle control system comprises a second relatively-rigid support member that contours about a wearer's leg and is connected to the upper attachment element of the form-fitting sock, wherein one relatively-rigid support member is connected to one side of the form-fitting sock and the second relatively-rigid support member is connected to the other side of the form-fitting sock.

According to a still further embodiment, the lever motion stabilizing strap has the second end adjustably attachable to the lateral side.

According to yet another embodiment, the lever motion stabilizing strap has the second end adjustably attachable to the medial side.

According to a still further embodiment, the lever motion stabilizing strap has the second end adjustably attachable to the front side.

In accordance with a still further embodiment of the invention, there is provided an ankle control system, comprising: a form-fitting brace, relatively-rigid support member, and a lever motion stabilizing strap. The form-fitting brace has opposing medial and lateral sides, opposing front and back sides, a foot portion, and an ankle portion having an upper attachment element. The relatively-rigid support member contours about a wearer's leg and is connected to the upper attachment element of the form-fitting brace. The lever motion stabilizing strap has a first end removably attachable to the foot portion of the form-fitting brace. The lever motion stabilizing strap is circumferentially wrapable around the foot portion to securely attach to the first end, and has a second end adjustably attachable to one of the lateral and medial sides. The lever motion stabilizing strap forms a circumferential restraint around the entire foot portion, which allows effective lever motion control of a foot.

According to yet another embodiment, the lever motion stabilizing strap is operatively configured as a lasso to restrict plantar flexion or plantar inversion through the lever action of a foot with respect to an ankle.

According to a still further embodiment, a single, straight and taut length of the stabilizing strap operatively spans between the foot portion and the upper attachment element to provide lever motion restraint.

In accordance with yet another embodiment of the present invention, there is provided a method of controlling an ankle. The first step of the method comprises providing (1) a form-fitting brace having opposing medial and lateral sides, a foot portion, and an ankle portion having an upper attachment element, (2) a first relatively-rigid support member that contours about a wearer's leg and is connected to the upper attachment element of the form-fitting brace, and (3) a lever motion stabilizing strap. The second step comprises fitting the form-fitting brace onto a foot. The third step comprises attaching a first end of the lever motion stabilizing strap to the foot portion of the form-fitting brace, and wrapping the lever motion stabilizing strap completely around the foot portion to securely attach an intermediate portion of the lever motion stabilizing strap to the first end of the lever motion stabilizing strap. The forth step comprises adjustably attaching a second end of the lever motion stabilizing strap to the upper attachment element of the form-fitting brace.

According to a still further embodiment, the lever motion stabilizing strap is operatively configured as a lasso to restrict plantar flexion or plantar inversion through the lever action of a foot with respect to an ankle.

According to yet another embodiment, the method comprises the step of completely encircling the foot portion with the lever motion stabilizing strap and attaching the second end such that a single, straight and taut length of the lever motion stabilizing strap operatively spans between the foot portion and the upper attachment element to provide lever motion restraint.

According to a still further embodiment, the step of providing comprises providing a second relatively-rigid support member that contours about a wearer's leg and is connected to the upper attachment element of the form-fitting brace, wherein the first relatively-rigid support member is connected to the lateral side of the form-fitting brace, and the second relatively-rigid support member is connected to the medial side of the form-fitting brace.

Further objects, features and advantages of the present invention will become apparent from the Detailed Description of Preferred Embodiments, which follows, when considered together with the attached Figures.

DETAILED DESCRIPTION

Figure 1:
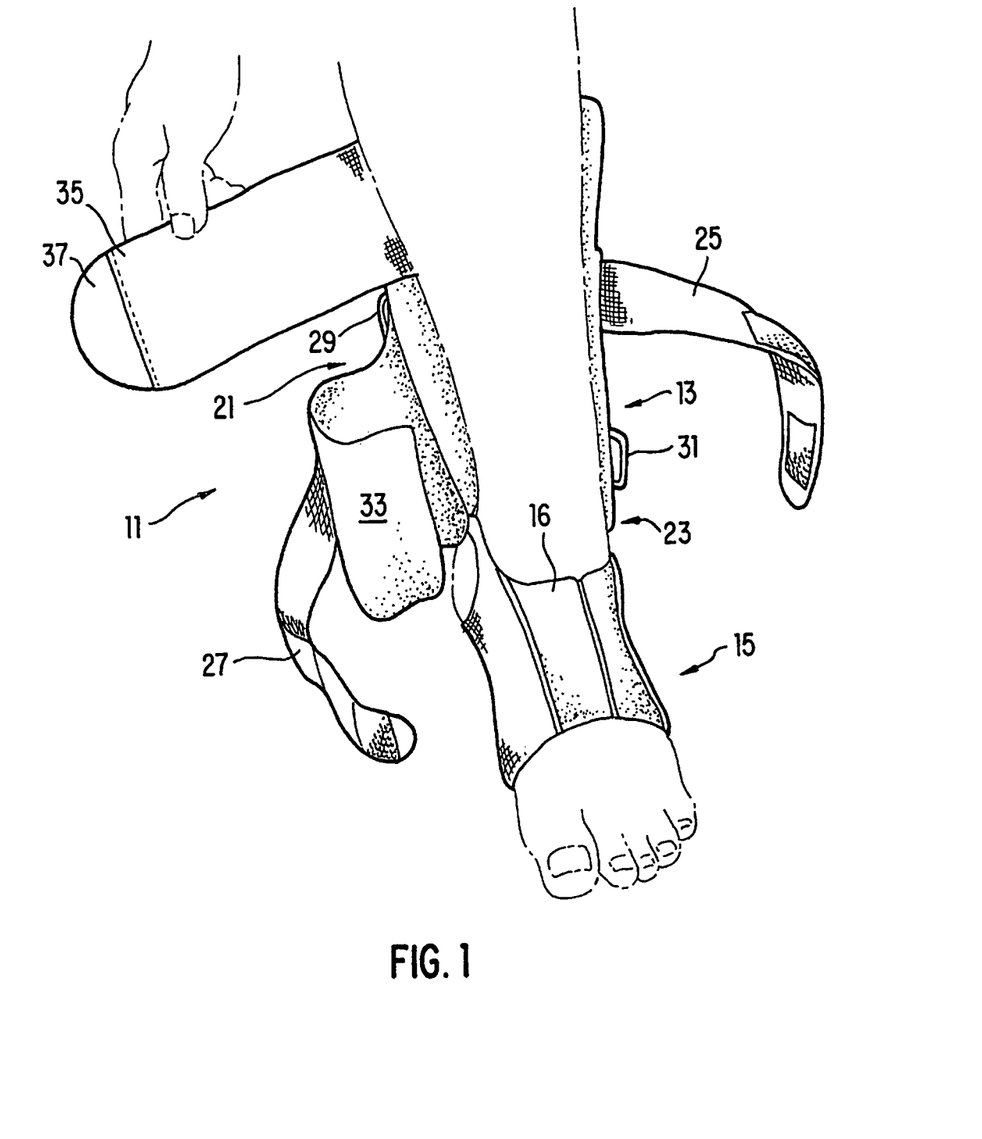
FIG. 1 is a right side perspective view of an ankle control system according to an embodiment of the present invention showing an open form-fitting sock with a collar in an "up" position, being worn on a left foot.
collar in an "up" position, being worn on a left foot.
Figure 5:
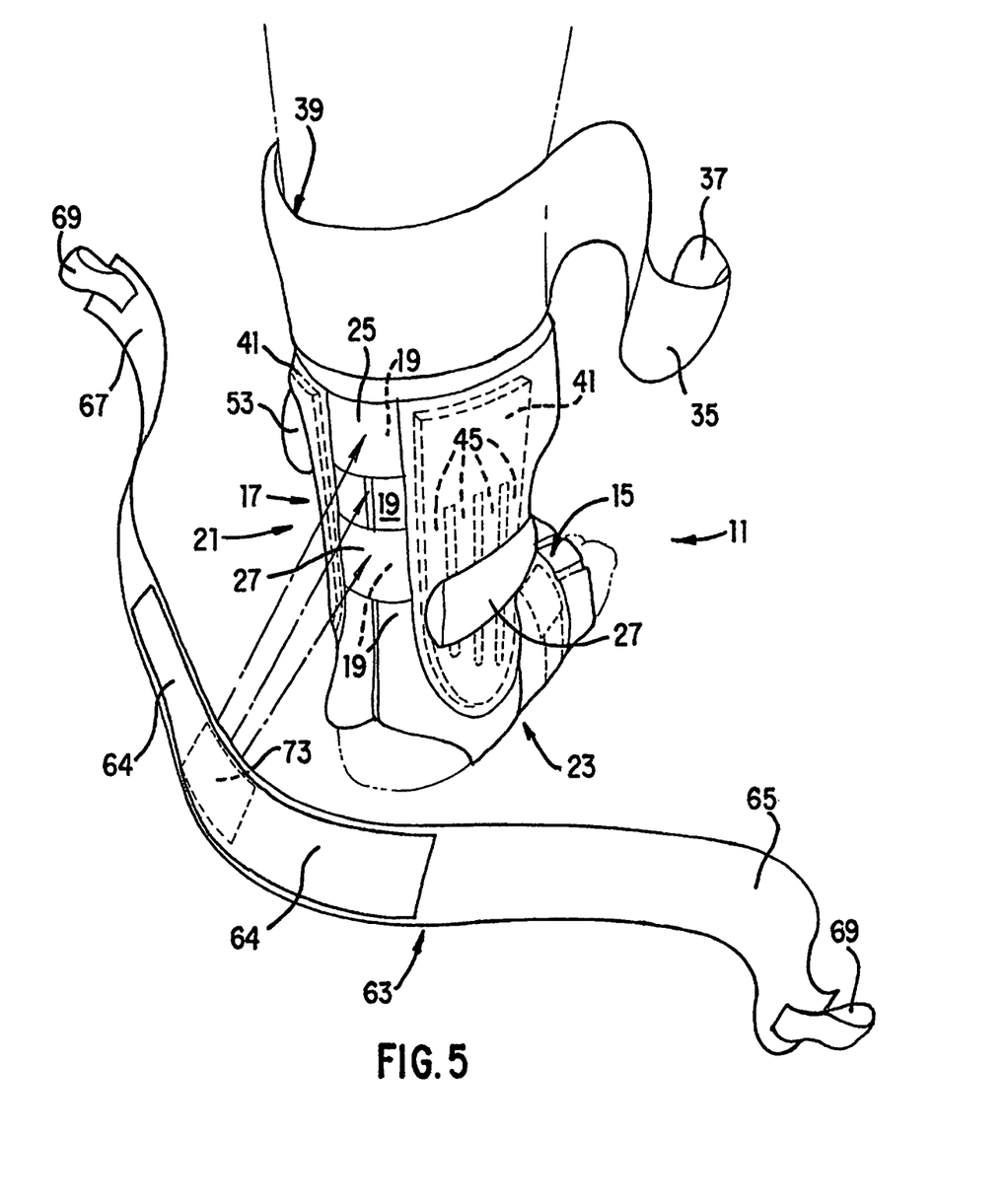
FIG. 5 is an exploded rear perspective view of the form-fitting sock and attached lever motion stabilizing strap shown in FIG. 4 with a stirrup strap according to an embodiment of the present invention.

In accordance with the present invention, FIG. 1 shows a form-fitting sock 11 having a open-faced ankle portion 13, and stretchable foot portion 15, having an arch portion 16. The form-fitting sock 11 has opposing medial 21 and lateral 23 sides, named as such in accordance with the medial and lateral sides of the ankle and lower leg of the person wearing the form-fitting sock 11—this designation depends on whether the form-fitting sock is worn on the right or left foot. As seen in FIG. 5, this form-fitting sock 11 also has a rear portion 17, which includes a vertical portion 19 along the Achilles tendon of the person wearing the form-fitting sock 11. Referring again to FIG. 1, a padded barrier 33, preferably comprising a two-sided fleece barrier 33 also is fixed, and preferably sewn, to one side of the ankle portion 13 of the form-fitting sock 11 but is not attached to the opposing (here in FIG. 1, lateral) side of the form-fitting sock 11. This barrier 33 folds over the wearer's foot under the closure straps 25 and 27 when worn. The barrier 33 as described allows easy access, added breathability, moisture wicking, and padding for comfort to the front of the wearer's ankle and lower leg. Finally, the form-fitting sock 11 has an elastic collar 35, which is shown in an "up" position in FIG. 1.

The foot portion 15 of the form-fitting sock 11 may be constructed from any material suitable for use while wearing a shoe, including any thin elastic material. In a preferred embodiment, the foot portion 15 and ankle portion 13 of the form fitting sock 11 are primarily made from a thin, highly elastic material of the type disclosed in U.S. Pat. No. 5,735,807 issued to Cropper, which is hereby incorporated by reference in its entirety. In particular, this material comprises a laminate material no greater than about 0.025 to 0.045 inch thickness and comprised of a polyurethane membrane no greater than about 0.001 inch thickness and a stretchable material covering said membrane, said material in a stretched state having the property of low active compressibility force and strong passive resistance to expansion substantially greater than the compressibility force. The exterior surface of the form-fitting sock 11 is made of a stretchable material, which is compatible for strap attachment with straps having hooks for a hook-and-loop-type attachment.

After the wearer inserts his or her foot into the foot portion 15, the form-fitting sock 11 can be closed by feeding opposing closure straps 25 and 27 (in an alternate preferred embodiment the bottom closure strap 27 is elastic) through respective opposing buckles 29 and 31 and folding the closure straps 25 and 27 back onto themselves at a desired tightness to affix the form-fitting sock 11 to the wearer's foot through a hook and loop fastening system. Specifically, the sides of these closure straps 25 and 27 have opposing hooks and loops to engage each other. The ends of the inelastic closure straps 25 and 27 feed through the buckles 29 and 31 and attach back onto themselves. There is enough hook material attached to the underside of the closure straps 25 and 27 to securely attach to the closure straps 25 and 27 over the form-fitting sock 11. The top closure strap 25 and bottom closure strap 27 are circumferential straps sewn down to the form-fitting sock 11 to provide secure attachment positions for the lever motion stabilizing strap 49 and stirrup strap 63. The closure straps 25 and 27 are shown fastened in FIG. 4.

Figure 2A:
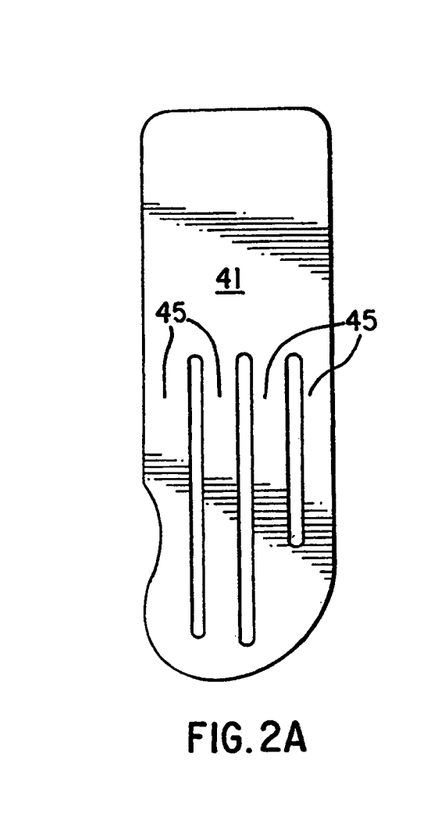
FIG. 2a is a plan view of a first preferred embodiment of a relatively-rigid support member according to the present invention.
Figure 2B:
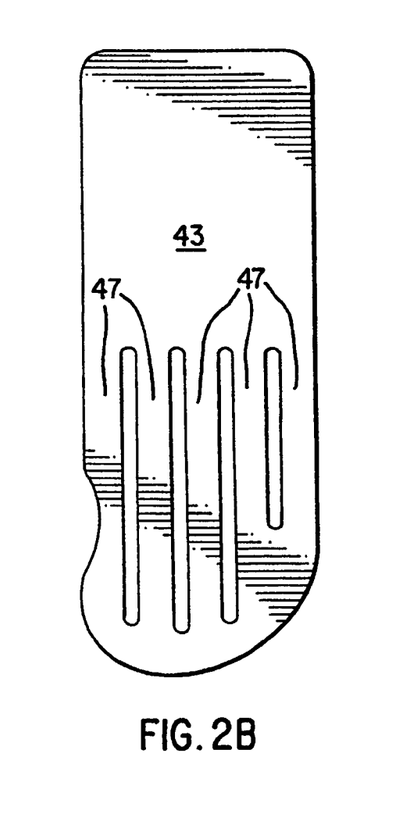
FIG. 2b is a plan view of a second preferred embodiment of a relatively-rigid support member according to the present invention.

FIGS. 2A and 2B show two embodiments of slotted support members 41, 43 according to the present invention. These semi-rigid support members 41, 43 each have one or more slots, in this embodiment, three and four, respectively, defining slats 45, 47, which resiliently buckle away from the plane defined by the support members 41, 43 when pressure is applied thereon. The support members 41, 43 are made from a thin resilient material, which is preferably a plastic like polycarbonate plastic, or any other suitable semi-rigid material. Support members, 41, 43 are preferably about 2.0 mm, or about 1/16 thick. The slats 45, 47 are cut into the resilient material so as to conform to the protruding shape of the medial and lateral malleolus to provide a contoured fit, as well as comfort and support through a full range of plantar-flexion and dorsi-flexion motions.

As depicted in FIG. 5, a small support member 41 is sewn inside each of the medial side 21 and the lateral side 23 of the ankle portion 13 of the form-fitting sock 11 and forcibly strapped against the malleolus of the wearer. Support members 41 are covered with a loop material on respective medial side 21 and lateral side 23 to allow attachment of the lever motion stabilizing strap 49 and stirrup strap 63. (See FIG. 5). Upon application of force from the closure straps 25 and 27, the slats 45 buckle to conform to the malleolus. The support members 41 thus provides resilient support to the ankle by contouring over the malleolus as pressure is exerted on the support members 41. For larger feet, a pair of support members 43 as shown in FIG. 2b may be used, whereby slats 47 similarly bend upon the application of force. The support members 41 in FIG. 5 are preferably positioned so that they rest at an angle against a portion of the medial and lateral malleolus, and preferably parallel to the wearer's foot. Various injuries, however, may call for positioning of the support members 41 at a more rear or forward position with respect to the malleolus.

Figure 2C:
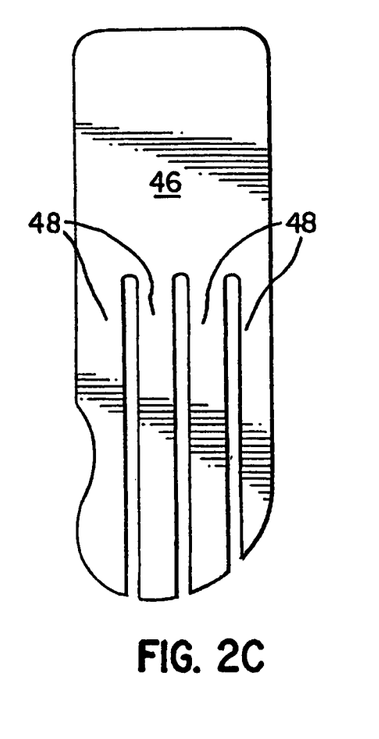
FIG. 2c is a plan view of a third preferred embodiment of a relatively-rigid support member according to the present invention.

In an alternate preferred embodiment seen in FIG. 2c, the support member 46 (or support members) comprises multiple, flexible, open-ended slots, which define finger-like structures 48 made of a similar material, which also conform to the protruding shape of the medial and/or lateral malleolus to provide a contoured fit.

Figure 3:
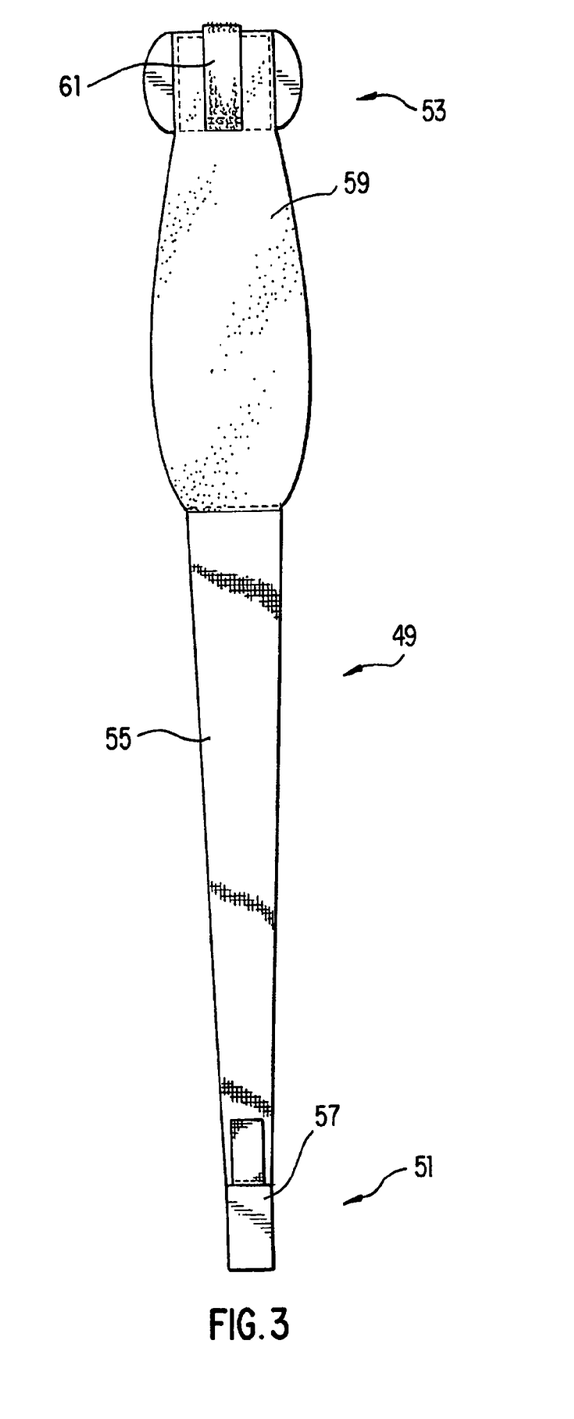
FIG. 3 is a plan view of the top side of a lever motion stabilizing strap according to an embodiment of the present invention.

FIG. 3 shows the top side of a lever motion stabilizing strap 49 having a tapered first end 51 and a wider second end 53, both of which attach to the form-fitting sock 11 by a hook and loop system. The underside of the second end 53 and both sides of the first end 51 have hook material. The The top side 59 of the second end 53 has loop (also known as pile) material. The lever motion stabilizing strap 49 is made from an inelastic material, preferably a polyamide (nylon), but can be of any inelastic material suitable for restraining the lever motion of a foot with respect to the ankle.

Figure 4:
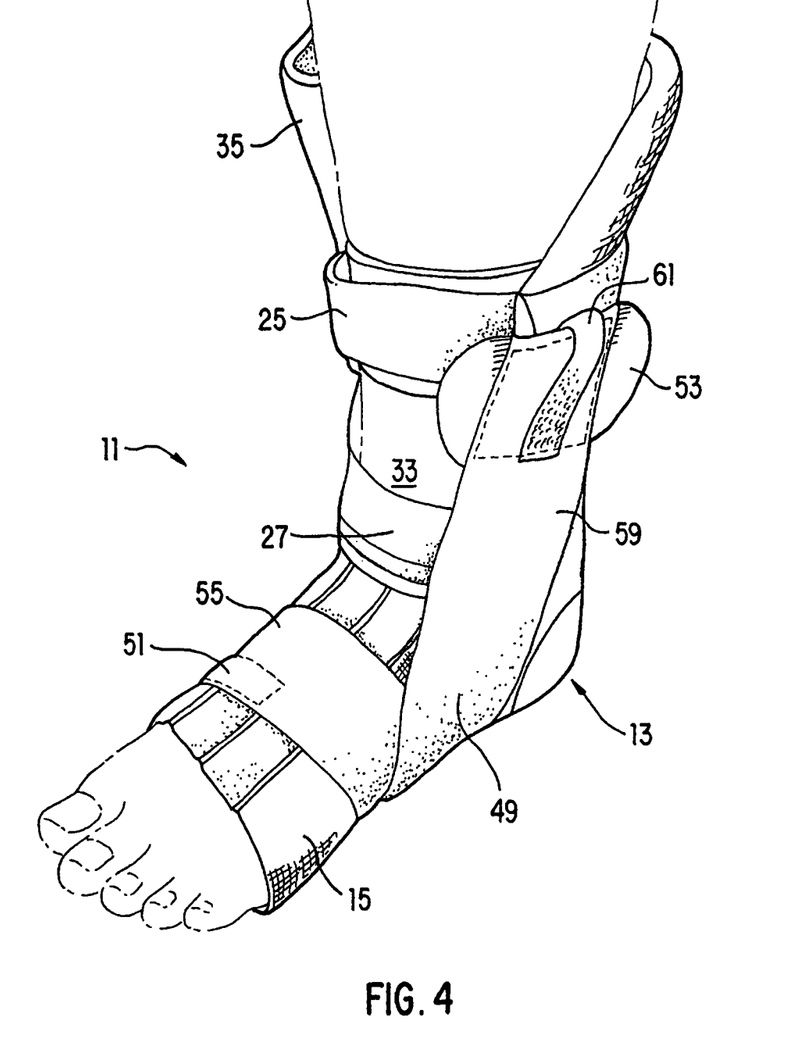
FIG. 4 is a left side perspective view of the form-fitting sock shown in FIG. 1 in a closed position but having the collar in an "up" position, and including the lever motion stabilizing strap of FIG. 3 attached in accordance with an embodiment of the present invention.

As seen in FIG. 4, after the form-fitting 11 is attached by the closure straps 25, 27, a lever motion stabilizing strap 49 is removably attached to the foot portion 15 of the form-fitting 11. This lever motion stabilizing strap 49 wraps circumferentially around the foot portion 15 and over an exposed side of the first end 51. Pile on an underside (not shown) of the middle portion 55 contacts hooks on top side 57 of first end 51 and becomes secured thereto. This forms a circumferential restraint around the entire foot portion 15, which allows effective lever motion control of the wearer's foot. The loop thereby created, coupled with the attached remaining second end 53 of the lever motion stabilizing strap 49, acts as a lasso to restrict plantar flexion/inversion through the lever action of the foot with respect to the ankle. Using finger loop 61, the lever motion stabilizing strap 49 is tightened and adjusted as needed. According to the sufficient and appropriate tightness to produce the desired control, the second end 53 is adjustably attached along lateral side 23 of form-fitting sock 11 through a hook and loop system. In addition, the lever motion stabilizing strap 49 is hook and loop compatible and is specifically attached to a distal end of medial side 21 of the foot portion 15 via a hook and loop fastener. The lever motion stabilizing strap 49 and finger loops 69 have exterior loop material to improve the attachment of the hook material on the stirrup strap 63, infra. The lever motion stabilizing strap 49 is long enough to wrap around the foot to the point of initial attachment. In a preferred embodiment, the lever motion stabilizing strap 49 attaches to itself by a fastener, in this embodiment, a hook and loop fastener, between separate portions of the strap 49, and again passes under the foot and attaches to the lateral side of the ankle (i.e., the lateral side 23 of frm-fitting sock 11, and/or the closure straps 25 and 27, depending upon the relative size of the wearer's foot and the fit of the form-fitting sock 11), via a hook tab, attached on the second end 53 of the lever motion stabilizing strap 49.

In an alternate preferred embodiment (not shown), the lever motion stabilizing strap 49 is attached to the medial side 21 but in a likewise circumferential fashion around the distal end of the foot portion 15 with initial attachment on the lateral side 23, to remedy and prevent eversion. In yet another alternate preferred embodiment two lever motion stabilizing straps 49 can be used in this fashion, one on each side of the foot.

As seen in FIG. 5, an inelastic stirrup strap 63 is adjustably and removably attached to the form-fitting sock 11 along the vertical portion 19. It is variously attachable along the vertical length of the Achilles tendon according to the positioning and type (e.g., high or low) of sprain sustained or protection required. Specifically, the stirrup strap 63 is variously attached by hook material on tab 73 to loop material on the closure straps 25, 27, to the exposed vertical portion 19 of the form-fitting sock 11, or to some combination thereof. The stirrup strap 63 has a first end 65, which beginning from the vertical portion 19, is sequentially wrapped around the medial side 23, over the arch portion 16 to opposing lateral side 21, and under foot portion 15 to allow adjustable attachment to the form-fitting sock 11 on the medial side 23. This controls the wearer's foot to prevent eversion.

The stirrup strap 63 also has a second end 67 sequentially wrapable from the vertical portion 19, around the lateral side 23, over the arch portion 16 to the opposing medial side 21, and under the foot portion 15 to allow adjustable attachment to the form-fitting sock 11 on its lateral side 23. This controls the wearer's foot to prevent inversion. Both the first end 65 and the second end 67 have finger loops 69 to allow easy tightening and adjustment of the stirrup strap 63, as needed. A patch 64 of loop material is sewn on both middle portions of the stirrup strap 63 to promote attachment of the ends 65 and 67, each of which have hook material on their undersides. Thus, the stirrup strap 63 having finger pull loops 69 is connected to the rear portion 17 of the form-fitting sock 11 and/or the closure straps 27 and 25 and is adjustable along the back of the form-fitting sock 11 over the Achilles tendon. The stirrup strap 63 has two ends 65 and 67 that are crossed over the top of the foot and then crossed under the foot and, by simultaneously pulling the stirrup strap 63 upward with the finger loops 69 and attaching to both medial 21 and lateral 23 sides of form-fitting sock 11, the stirrup strap 63 prevents eversion and inversion. A particular advantage of the stirrup strap 63 is the ability to remedy and prevent "high" ankle sprains.

Figure 6:
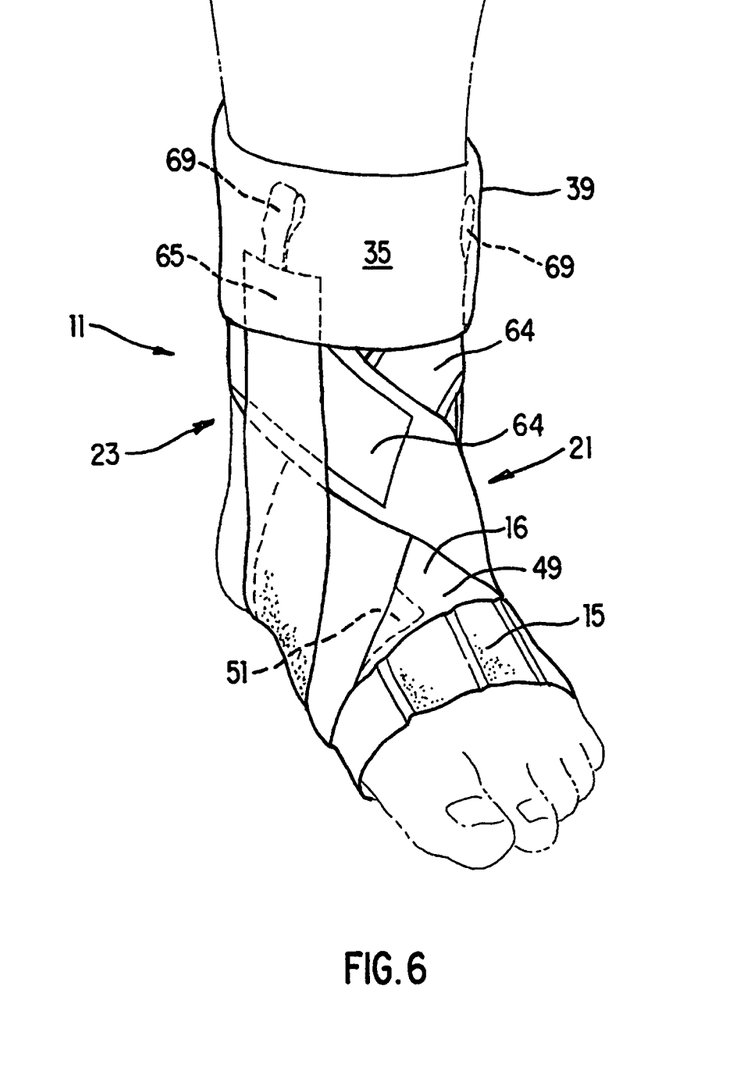
FIG. 6 is a right side perspective view of the form-fitting sock, lever motion stabilizing strap, and the stirrup strap shown in FIG. 5, wherein the stirrup strap is attached and the collar is in the "down" position.

As seen in FIG. 6, collar 35 folds to an inverted "down" position over strap ends 53, 65, and 67. This secures the various strap ends 53, 65, and 67 in place after their adjustment, by a hook and loop attachment system between the collar end 37 (FIGS. 1 and 5) and its outside lateral portion 39. Thus, the collar 35 that is attached to the top of the form-fitting sock 11 is designed to roll over the attached straps 49, 63 to secure it. This allows an easy way of securing the straps 49, 63 without the bulk and clumsiness of a long circumferential strap.

Notwithstanding collar 35, in an alternate preferred embodiment, a securing strap (not shown) is attached to the midsection of a strap such as stirrup strap 63. This securing strap wraps around the circumference of the ankle at the upper portion of the form-fitting sock 11 and attaches to itself by way of hook and loop fasteners. This strap, like the collar 35, secures all of the straps in place.

It is to be understood that to those skilled in the art that while certain embodiments of the present invention have been described and shown herein, additions, deletions, substitutions, modifications and improvements may be made without departing from the scope of the invention. For example, various hook and loop fasteners have been described. One of ordinary skill in the art would readily understand that the position of hook members and loop members of the preferred embodiments may be readily reversed without impairing the function of the present invention.

The invention is therefore not to be limited to the embodiments described and illustrated herein, but is to be determined solely from the appended claims.

I claim:

1. A method for controlling an ankle, comprising:
    providing:
        a form-fitting sock or brace having opposing medial and lateral sides, a foot portion, and an ankle portion having an upper attachment element,
        a first relatively-rigid support member that contours about a leg of a wearer and is connected to the upper attachment element of the form-fitting sock or brace, and
        a lever motion stabilizing strap;
    placing the form-fitting sock or brace on afoot of the wearer;
    attaching a first end of the lever motion stabilizing strap to a distal end of the foot portion of the form-fitting sock or brace, and wrapping the lever motion stabilizing strap circumferentially around the distal end of the foot portion, an intermediate portion of the lever motion stabilizing strap contacting a portion of the lever motion stabilizing strap circumferentially surrounding the distal end of the foot portion;
    extending the intermediate portion of the lever motion stabilizing strap substantially linearly between a side of the foot portion of the form-fitting sock or brace, over an ankle between the foot and the leg, and an attachment location of the upper attachment element of the form-fitting sock or brace, with the upper attachment element surrounding an upper portion of the ankle or a portion of the leg adjacent to the ankle; and
    adjustably attaching a second end of the lever motion stabilizing strap to the attachment location of the upper attachment element of the form-fitting sock or brace surrounding the leg.

2. The method of claim 1, wherein wrapping the lever motion stabilizing strap completely around the distal end of the foot portion of the form-fitting sock or brace comprises fitting a lever motion stabilizing strap operatively configured as a lasso around the distal end of the foot portion to restrict at least one of plantar flexion or plantar inversion through the lever action of the foot with respect to an ankle associated with the foot.

3. The method of claim 1, further comprising:
    completely encircling the foot portion of the form-fitting sock or brace with the lever motion stabilizing strap and attaching the second end of the lever motion stabilizing strap such that a single, straight and taut length of the lever motion stabilizing strap operatively spans between the foot portion of the form-fitting sock or brace and the upper attachment element of the form-fitting sock or brace.

4. The method of claim 1, wherein providing comprises providing a second relatively-rigid support member that contours about the leg of the wearer and is connected to the upper attachment element of the form-fitting sock or brace, wherein the first relatively-rigid support member is connected to the lateral side of the form-fitting sock or brace, and the second relatively-rigid support member is connected to the medial side of the form-fitting sock or brace.

5. The method of claim 1, wherein at least one of attaching the first end and adjustably attaching the second end of the lever motion stabilizing strap comprises securing at least one of the first end and the second end of the lever motion stabilizing strap with a hook and loop material.

6. The method of claim 1, wherein attaching the first end of the lever motion stabilizing strap includes securing either a hook material or a loop material on a first side of the lever motion stabilizing strap to the distal end of the foot portion of the form-fitting sock or brace, and either the hook material or the loop material on a second side of the lever motion stabilizing strap to a mid-portion of the lever motion stabilizing strap once the lever motion stabilizing strap is wrapped around the foot portion of the form-fitting sock or brace.

7. The method of claim 1, wherein attaching the first end of the lever motion stabilizing strap comprises attaching a tapered end of the lever motion stabilizing strap.

8. The method of claim 1, wherein attaching the first end of the lever motion stabilizing strap to the distal end of the foot comprises introducing the distal end of the foot into at least one loop defined by the lever motion stabilizing strap.

9. The method of claim 1, wherein adjustably attaching the second end of the lever motion stabilizing strap comprises adjustably attaching the second end to a lateral side of the upper attachment element of the form-fitting sock or brace.

10. The method of claim 1, wherein adjustably attaching the second end of the lever motion stabilizing strap comprises adjustably attaching the second end to a medial side of the upper attachment element of the form-fitting sock or brace.

11. The method of claim 1, wherein adjustably attaching the second end of the lever motion stabilizing strap comprises adjustably attaching the second end to a front side of the upper attachment element of the form-fitting sock or brace.

12. The method of claim 1, wherein attaching the first end of the lever motion stabilizing strap, wrapping the lever motion stabilizing strap and adjustably attaching the second end of the lever motion stabilizing strap comprise orienting the lever motion stabilizing strap such that a single, straight and taut length of the lever motion stabilizing strap operatively spans between the foot portion and the upper attachment element of the form-fitting sock or brace.

13. The method of claim 12, wherein orienting the lever motion stabilizing strap includes providing lever motion restraint.

14. A method for controlling an ankle, comprising:
using, wearing, or providing at least:
  a form-fitting sock or brace having opposing medial and lateral sides, a foot portion, and an ankle portion having an upper attachment element, and
  a lever motion stabilizing strap;
placing the form-fitting sock or brace onto a foot;
attaching a first end of the lever motion stabilizing strap to a distal end of the foot portion of the form-fitting sock or brace, and wrapping the lever motion stabilizing strap completely around the distal end of the foot portion, an intermediate portion of the lever motion stabilizing strap extending from a wrapped portion of the lever motion stabilizing strap;
extending the intermediate portion of the lever motion stabilizing strap substantially linearly from the wrapped portion of the lever motion stabilizing strap, over an ankle adjacent to the foot, to an attachment location of the upper attachment element of the form-fitting sock or brace surrounding an upper portion of the ankle or a portion of a leg adjacent to the ankle, on an opposite side of the ankle from the foot; and
adjustably attaching a second end of the lever motion stabilizing strap to the upper attachment element of the form-fitting sock or brace.

15. The method of claim 14, wherein wrapping the lever motion stabilizing strap completely around the distal end of the foot portion of the form-fitting sock or brace comprises fitting a lever motion stabilizing strap operatively configured as a lasso around the distal end of the foot portion to restrict at least one of plantar flexion or plantar inversion through the lever action of the foot with respect to an ankle associated with the foot.

16. The method of claim 14, further comprising:
completely encircling the foot portion of the form-fitting sock or brace with the lever motion stabilizing strap; and
attaching the second end of the lever motion stabilizing strap to the attachment location of the upper attachment element of the form-fitting or brace such that a single, straight and taut length of the lever motion stabilizing strap operatively spans between the foot portion and the upper attachment element of the form-fitting sock or brace.

17. The method of claim 14, wherein attaching the first end of the lever motion stabilizing strap comprises attaching a tapered end of the lever motion stabilizing strap.

18. The method of claim 14, wherein attaching the first end of the lever motion stabilizing strap comprises introducing the distal portion of the foot into at least one loop defined by the lever motion stabilizing strap.

19. The method of claim 14, wherein adjustably attaching the second end of the lever motion stabilizing strap comprises adjustably attaching the second end to a lateral side of the form-fitting sock or brace.

20. The method of claim 14, wherein adjustably attaching the second end of the lever motion stabilizing strap comprises adjustably attaching the second end to a medial side of the upper attachment element of the form-fitting sock or brace.

21. The method of claim 14, wherein adjustably attaching the second end of the lever motion stabilizing strap comprises adjustably attaching the second end to a front side of the upper attachment element of the form-fitting sock or brace.

22. The method of claim 14, wherein attaching the first portion of the lever motion stabilizing strap, wrapping the lever motion stabilizing strap and adjustably attaching the second end of the lever motion stabilizing strap comprise orienting the lever motion stabilizing strap such that a single, straight and taut length of the lever motion stabilizing strap operatively spans between the foot portion and the upper attachment element of the form-fitting sock or brace.

23. The method of claim 22, wherein orienting the lever motion stabilizing strap includes providing lever motion restraint.

24. A method for controlling an ankle, comprising:
extending an ankle-spanning portion of a stabilizing strap substantially linearly from a first end adjacent to a foot-securing portion of the stabilizing strap that at least partially surrounds a foot, over an ankle adjacent to the foot, to a second end adjacent to a leg-securing portion of the stabilizing strap; and
securing the second end of the ankle-spanning portion of the stabilizing strap in place over an upper portion of the ankle or over a portion of a leg adjacent to the ankle, on an opposite side of the ankle from the foot.

25. The method of claim 24, further comprising:
positioning the foot-securing portion of the stabilizing strap beneath the foot.

26. The method of claim 24, further comprising:
securing the foot-securing portion of the stabilizing strap in place around the foot.

27. The method of claim 26, wherein securing the foot-securing portion of the stabilizing strap comprises wrapping the foot-securing portion around the foot.

28. The method of claim 26, wherein securing the foot-securing portion of the stabilizing strap comprises securing the foot-securing portion circumferentially around the foot.

29. The method of claim 26, further comprising:
securing the first end of the ankle-spanning portion of the stabilizing strap to the foot-securing portion of the stabilizing strap.

30. The method of claim 24, wherein extending the ankle-spanning portion of the stabilizing strap comprises extending the ankle-spanning portion from the foot-securing portion at a location adjacent to a side of the foot.

31. The method of claim 24, wherein extending the ankle-spanning portion of the stabilizing strap and securing the second end of the ankle-spanning portion of the stabilizing strap in place are effected without providing direct support to the ankle.

32. The method of claim 24, wherein extending the ankle-spanning portion of the stabilizing strap and securing the second end of the ankle-spanning portion of the stabilizing strap in place are effected without wrapping the ankle-spanning portion around the ankle.

33. The method of claim 24, wherein extending the ankle-spanning portion of the stabilizing strap and securing the second end of the ankle-spanning portion of the stabilizing strap in place are effected in a manner that generates sufficient tension in the ankle-spanning portion to impart external support to the ankle.

* * * * *